United States Patent
Szpak et al.

(10) Patent No.: US 9,651,038 B2
(45) Date of Patent: May 16, 2017

(54) PULSATION SUPPRESSING AIR FLOW SYSTEM FOR AN AIR SAMPLING INSTRUMENT

(71) Applicant: Met One Instruments, Inc., Grants Pass, OR (US)

(72) Inventors: Gerald A. Szpak, Grants Pass, OR (US); Thomas L. Pottberg, Grants Pass, OR (US)

(73) Assignee: Met One Instruments, Inc., Grants Pass, OR (US)

( * ) Notice: Subject to any disclaimer, the term of this patent is extended or adjusted under 35 U.S.C. 154(b) by 239 days.

(21) Appl. No.: 14/500,539

(22) Filed: Sep. 29, 2014

(65) Prior Publication Data

US 2015/0089999 A1   Apr. 2, 2015

Related U.S. Application Data

(60) Provisional application No. 61/883,465, filed on Sep. 27, 2013.

(51) Int. Cl.
*G01N 1/24* (2006.01)
*F04B 39/00* (2006.01)
*F04B 49/08* (2006.01)
*G01N 33/00* (2006.01)

(52) U.S. Cl.
CPC ...... *F04B 39/0061* (2013.01); *F04B 39/0055* (2013.01); *F04B 49/08* (2013.01); *G01N 1/24* (2013.01); *G01N 33/0027* (2013.01)

(58) Field of Classification Search
CPC .............. F04B 39/0027; F04B 39/0055; F04B 39/0061; G01N 1/2273; G01N 1/24; G01N 15/06; G01N 21/53; G01N 2015/0693

See application file for complete search history.

(56) References Cited

U.S. PATENT DOCUMENTS

| | | | |
|---|---|---|---|
| 4,141,240 A * | 2/1979 | Usui | G01F 1/32 73/114.42 |
| 4,257,746 A * | 3/1981 | Wells | G01N 1/2273 417/43 |
| 5,295,790 A | 3/1994 | Bossart et al. | |
| 5,892,160 A | 4/1999 | Hall | |
| 2004/0247457 A1* | 12/2004 | Kim | F04B 35/045 417/312 |
| 2015/0063982 A1* | 3/2015 | Pariseau | F04D 19/022 415/115 |

* cited by examiner

*Primary Examiner* — Blake A Tankersley
(74) *Attorney, Agent, or Firm* — Thomas Schneck

(57) ABSTRACT

A pulsation and particle suppressing continuous air flow system for air sampling instruments, particularly particle counters. An air pump occupies a portion of a sealed vacuum housing, with the other portion of the housing forming a surge chamber used to damp surges as the air pump attempts to pump air towards an air outflow port through an outflow pipe. The unoccupied volume of the surge chamber dampens or dilutes the surges at an air inflow port of the housing that is associated with an air sampling instrument, such as a particle counter. The air outflow port is associated with a filter for trapping particles originating inside of the air pump and associated motor while the interior of the housing itself traps particles originating outside of the air pump and motor.

19 Claims, 6 Drawing Sheets

PULSATION SUPPRESSING AIR FLOW SYSTEM FOR AN AIR SAMPLING INSTRUMENT

CROSS-REFERENCE TO RELATED APPLICATION

This application claims priority from provisional application Ser. No. 61/883,465, filed Sep. 27, 2013.

BACKGROUND ART

Certain scientific instruments, such as airborne particle counters, use a vacuum pump to sample aerosols by pulling an air stream through the sampler. The vacuum pump can be built-in or connected externally. The vacuum pump draws the sample air into the particle sensor where particles are sized and counted, sometimes using optics and sometimes using irradiation or other techniques. Particle counter vacuum pumps have unique requirements. They must be reliable over a long period of time, support flow control typically using DC power, have little or no flow pulsations for continuous flow, and they must not shed particles.

Reciprocating pumps, such as diaphragm or piston pumps offer long life and flow control. These pumps can also produce a high vacuum by positive displacement of air. However, reciprocating pumps have excessive flow pulsations and they shed particles. Consequently, reciprocating pumps have had limited success in the particle counter industry.

Rotary vane pumps offer high vacuum and good flow control. However, these pumps have limited life because vanes fail. They also have flow pulsations and they generate particles.

Centrifugal pumps or blowers offer long life, flow control and continuous flow. However, these pumps have a weak air flow characteristic due to low vacuum. They also generate particles.

Most pump technologies produce flow pulsations or surges in the sample flow path. These pulsations degrade particle sensor resolution and therefore reduce particle counter measurement accuracy. Also, most pump technologies generate particles inside and outside the flow path. Particles inside the flow path can easily be filtered with an exhaust filter. Particles shed outside the flow path, such as in motor brushes, bearings, and moving parts of the pump are problematic. These particles contaminate the sample aerosol when they escape through vents or gaps in the instrument enclosure. An object of the invention is to devise a pulsation and particle suppressing air flow system for an air sampling instrument.

Efforts have been made in the prior art to establish a continuous smooth volumetric flow through an air sampling instrument. For example, in U.S. Pat. No. 5,295,790 C. Bossart et al. teach a portable sampling pump apparatus including a flow control mechanism having a flowmeter for feedback control for the pump motor. The pump apparatus includes an electric motor, a pump operably driven by the electric motor, a laminar flow element positioned in a flow path of the pump, a pressure transducer for sensing a pressure drop across the laminar flow element and for producing an electrical signal that is directly and linearly proportional to the volumetric flow rate through the pump, and a motor control circuit which uses the electrical signal to control the voltage applied to the motor and to thereby regulate the flow of the pump.

In U.S. Pat. No. 5,892,160 P. Hall teaches an air or gas sampling device that utilizes a small tube calibrated under isothermal conditions. The relationship of pressure at the input end of the tube to flow is plotted and stored in a microprocessor for comparison with pressure monitored during sample pumping. Pulsations in flow caused by the air or gas pump can be neutralized by a damper comprising a small chamber having a diaphragm for one wall.

An object of the invention was to devise an improved continuous air flow system for an air sampling instrument with suppressed pulsations and particle release.

SUMMARY OF INVENTION

We have devised an air flow system that solves flow pulsation and particle shedding issues in air sampling instruments, particularly particle counters. The solution involves enclosing a vacuum pump in a sealed housing to create a low pressure surge chamber in a space within the housing not occupied by the pump in order to dilute or buffer the pulsations while also trapping particles. The pump pulls low pressure air inside the housing through an air intake port. Pump surges are not communicated by pulled air directly to the instrument, but only indirectly through the surge chamber. Exhaust air from the pump is directed out of the housing through a pipe. An optional restrictor at the air intake port of the housing works with the volume of air into the housing to throttle pulsating flow at the pump air intake port into the surge chamber. An output filter prevents particles from escaping through the output flow path. The output filter can be mounted inside the pump enclosure or outside the enclosure.

DETAILED DESCRIPTION

Figure 1:
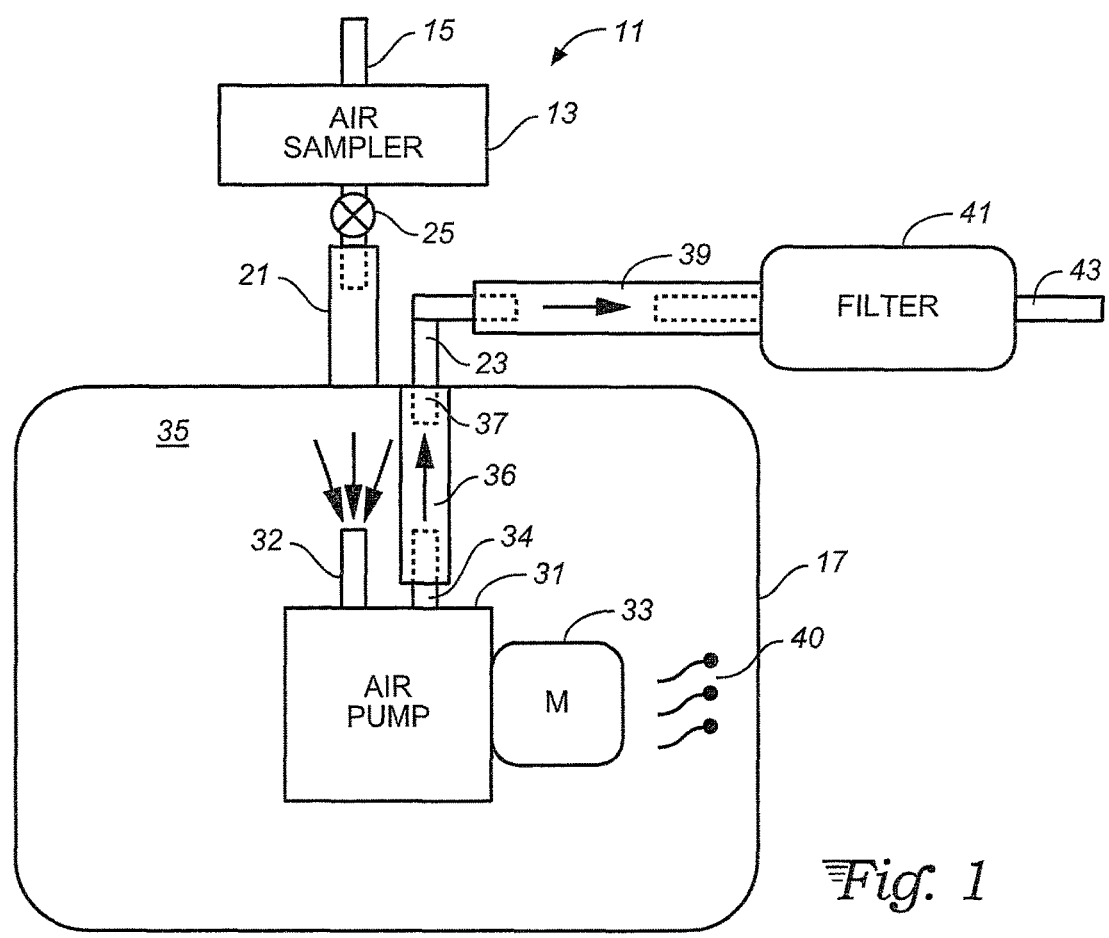
FIG. 1 is a plan view of a particle suppressing air flow system for an air sampling instrument of the present invention.

With reference to FIG. 1, a pulsation suppressing airflow system 11 features a closed housing 17 that is a sealed volume where an air pump 31 is located, driven by a motor 33. The housing 17 is airtight and may be fabricated of metal with doors and apertures having appropriate airtight seals, not shown. The air pump 31 is supported in the housing so that it occupies only a portion of the housing with the remainder of the housing being surge chamber 35 that occupies a volume which is typically at least the size of the pump 31 and its associated motor 33, preferably a larger volume. Pump 31 may be centrifugal pump or rotary radial vane pump, or a reciprocating pump, all having some extent of pulsations. The surge chamber 35 is the zone where pulsating air associated with the pump will be damped so that pulsations are suppressed and not communicated outside of the housing through an inflow port. The housing 17 has an air inflow port 21 that is spaced a distance from the air pump where a continuous, nonpulsating flow of air is desired. The distance spans a portion of the unoccupied space of the housing that forms the surge chamber. The air inflow port 21 must have a sufficiently small diameter to allow air pump 31 to develop low pressure, such as vacuum pressure, in housing 17. Connected to air inflow port 21 is an air sampling instrument 13, such as a sensitive particle sensor or counter where a continuous, surge suppressed stream of air is needed. Since such instruments typically count particles of the order of parts per billion in real time, smooth continuous airflow is essential because flow pulsations degrade or worsen size resolution. In international standard ISO 21501-4, size resolution is defined as one standard deviation of the measured size distribution of monodisperse calibration particles, expressed as a percentage of the mean size of the monodisperse calibration particles. Flow pulsations tend to broaden the size resolution and as a result, reduce the instruments ability to differentiate two particles that are near the same size.

The air sampling instrument 13, such as a particle counter, has an air intake 15, open to ambient air, where it is desired that a smooth flow of air enter the instrument 13. A flowmeter 25 is typically interposed between the air inflow port 21 of the housing and air sampling instrument 13 for measuring volumetric air flow. The flowmeter usually includes a temperature sensor for flow regulation. Flowmeters actually measure mass flow that can be converted to volumetric flow using temperature and barometric pressure information. On the other hand, this information is not required for particle counters with volumetric flow sensors.

The air pump 31 may be a centrifugal pump or a rotary vane pump driven by motor 33 which is typically a DC pulsewidth modulated motor. On the other hand, a pulsation suppressing housing would allow use of a reciprocating pump, such as a piston or displacement pump which has the advantage of longer life and higher vacuum. However, a reciprocating pump will produce greater pulsations and require a larger housing than a vane pump. Smaller pulsations are produced with a rotary vane pumps and centrifugal blowers driven by a DC pulse modulated motor.

The air pump 31 has a pump inlet 32 where pulsating air in the surge chamber 35 is received. The air pump evacuates the housing 17 through outlet 34 into pipe 36 and to the air exit airflow port 23 of housing 17. By receiving air in the pump inlet 32 which is spaced a distance away from air inflow port 21, the surge chamber 35 has a reduced pressure typical of a laboratory vacuum chamber. A sealed pipe 36 connects a housing outlet feed-through port 37 with an air exit airflow port 23 of the housing, with a feed-through maintaining the vacuum condition of housing 17. A conduit 39 connects the air exit outflow port 23 to an output filter 41 and there removes any particles coming from the interior of the pump and motor combination. Other particles 40 from the exterior of the pump and motor combination that are shed are trapped inside of housing 17 and have no escape path. The output filter 41 has a filter output conduit 43 where filtered air is returned to the ambient environment.

In operation, the vacuum condition existing in the surge chamber 35 due to a pump pulls air into the instrument 13, such as a particle sensor or counter. The air inflow port 21 has a small diameter so that the air pump 31 is not overwhelmed, but is allowed to pull a desired air flow to a laboratory vacuum pressure as measured by the flowmeter 25. If a greater flow is desired, the pump velocity can be increased or the diameter of the air inflow port 21 can be increased.

Figure 2:
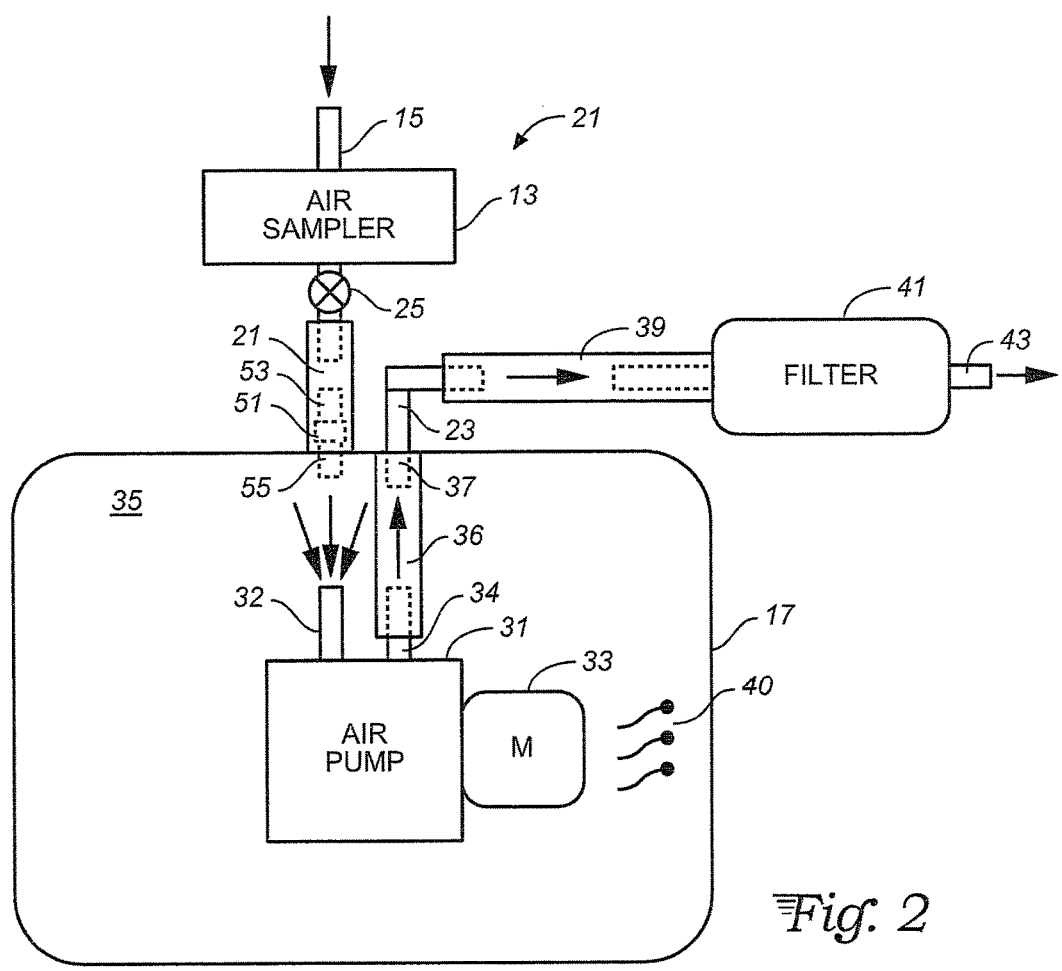
FIG. 2 is a plan view of a first alternate embodiment particle suppressing air flow system for an air sampling instrument of the invention with a flow restrictor.

With reference to FIG. 2, the pulsation suppressing system is essentially the same as shown in FIG. 1, except that a restrictor 51 is placed in the air inflow port 21 in a manner so that only the restrictor output 55 penetrates housing 17 in an airtight manner. The restrictor 51 has an input 53 that is open to airflow within air inflow port 21. Essentially, the restrictor 51 is a smaller diameter pipe than the air inflow port 21 that limits airflow into the surge chamber 35 to a desired amount. Each time there is a stroke of the pump 31 or a vane rotation, there is a vacuum surge inside of surge chamber 35. Pump surges develop a pressure drop across the restrictor 51. The pump inlet 32 pulls air from the chamber 35 rather than through the restrictor 51 because the chamber is unrestricted. Pressure at the pump inlet 32 will vary considerably. Pressure in the surge chamber will vary much less. Pressure on the instrument side of the restrictor will vary very little. Therefore, the particle sensor will have smooth continuous flow.

The restrictor 51 experiences a smaller amount of surge than air being pumped into the pump inlet 32 because the restrictor has a diminished input orifice and throughput, i.e., has restricted flow into the chamber. A surge chamber 35 provides a volumetric dilution of the surge from the restrictor 51. The result is that surges inside of air pump 31 are suppressed, with a smoother air flow through restrictor 51.

Figure 3:
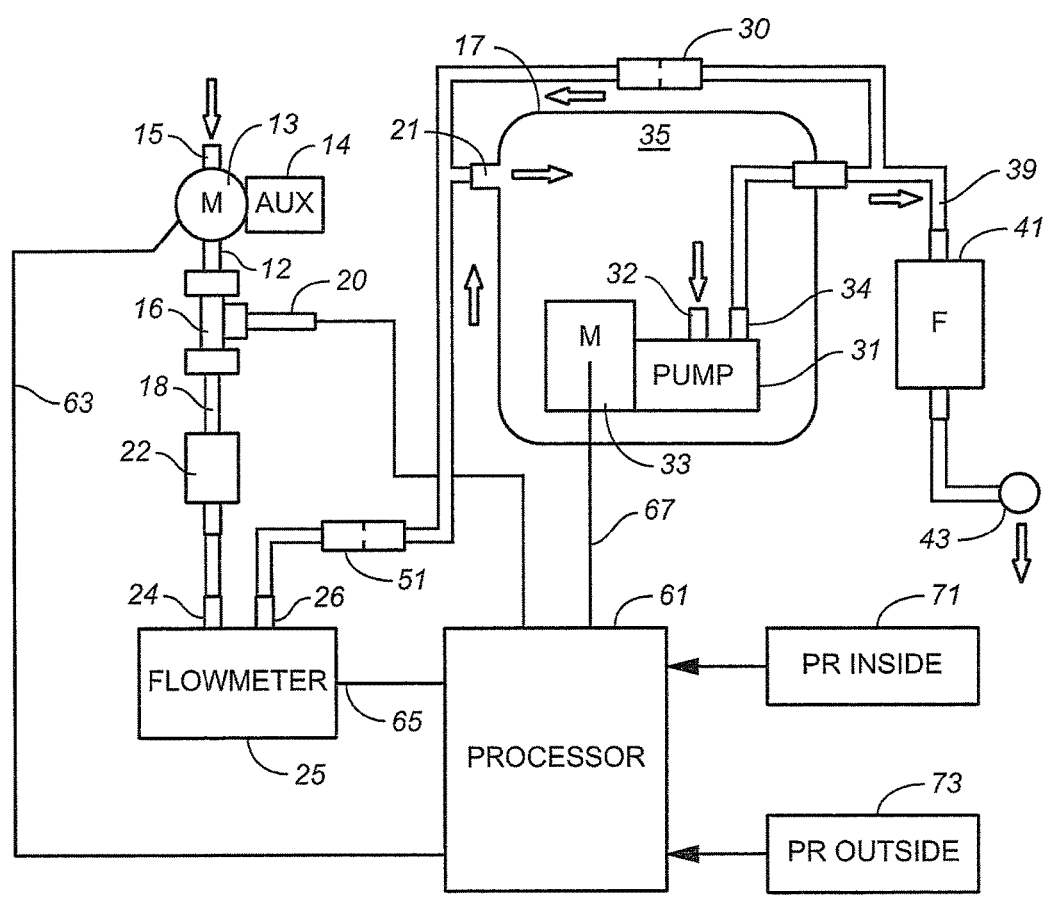
FIG. 3 is an electrical control diagram for the system of FIG. 2.

In FIG. 3, the electronic components of the system may be seen. The air sampling instrument 13 with an auxiliary instrument 14 is connected to receive air through an air intake port 15, as previously described. The auxiliary instrument 14 may be a device that uses the sampled air for a particular purpose, such as chemical processing. The air sampling instrument 13 may be connected to a temperature probe 16 through a probe inlet 12, with air exiting through a probe outlet 18 towards the flowmeter 25 through a coarse particle filter 22 that removes larger particles without restricting flow to any significant extent. The temperature probe measures the sample air stream temperature.

Mass flow measured by a flowmeter can be converted to volumetric flow using temperature and pressure information. An outside pressure measurement is made with outside pressure sensor 73 connected to electronic processor 61. A signal from the flowmeter 25 is connected along the flowmeter signal line 65 to the processor 61. Air flow through the flowmeter 25 exits through output port 26 to the restrictor 51 previously described in FIG. 2. From the restrictor, air flows into the housing 17, pulled by the pump 31, driven by motor 33. Air into the housing reaches the surge chamber 35 where surge is dissipated in the unoccupied portion of the volume within the housing that constitutes the surge chamber. The pump 31 creates a vacuum condition in the surge chamber pulling air through the flowmeter 25 and the air sampling instrument in a pulsation suppressed manner.

A feature not previously described is bypass orifice 30 which may be a one way valve such as a flap valve that equalizes pressure when the air inflow port 21 is blocked. For example, in shipping the pump housing, a rubber cap may be installed on the housing air inflow port 15. If the cap is not removed and the pump 31 is started, the resulting vacuum might make it impossible to remove the cap even after the pump is stopped. The bypass orifice 30 allows pressure equalization in that situation so that the cap can be removed. The bypass orifice is a small orifice that lets pressure equalize. Some pumps have check valves so they hold a vacuum when one blocks the inlet. The orifice leaks a small percentage of the air flow from output to input to equalize the pressure. A check valve for the bypass will not be ideal because it would shunt too much air and reduce pump capacity, although a check valve would be economical. Air being exhausted by the pump 31 exits through the pump outlet 34 toward the outlet feedthrough port 37 towards the output particle filter 41 and the filter output conduit 43. The output filter 41 should filter below the sensitivity limit of the particle counter. For example, the filter in a 0.3 um particle counter must remove a high percentage of 0.3 um particles and larger. Pressure inside of the pump module is measured by a pressure sensor 71 that feeds a first pressure signal to processor 61 while the ambient pressure outside of housing 17 is measured by the outside pressure sensor 73 which has an output signal also connected the processor 61 so that a differential pressure measurement may be computed. It is possible to control flow into the surge chamber 35 by means of pressure differences, rather than a flowmeter, assuming that temperature of the inflowing air stream is taken into account. The processor 61 computes actual air flow versus desired air flow and can send a signal along line 67 to motor 33 to adjust the pump rate of air pump 31. This is essentially a feedback system for achieving a desired continuous airflow through the air sampling instrument.

Figure 4:
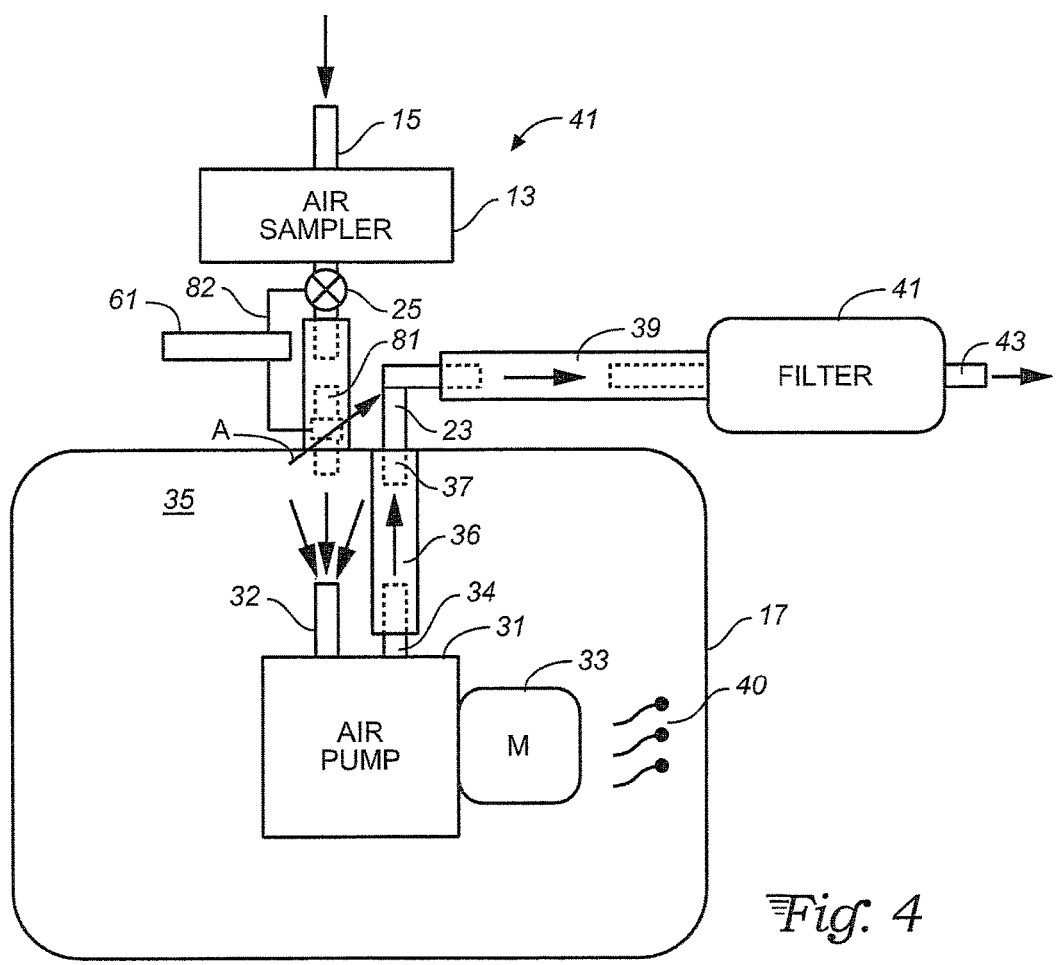
FIG. 4 is a plan view of a second alternate embodiment particle suppressing air flow system for an air sampling instrument of the invention with a variable flow restrictor controlled by a flowmeter.

FIG. 4 is similar to FIG. 2 except that the restrictor is variable restrictor 81 that may be controlled by the processor 61. The variable restrictor may be a variable valve with variability indicated by arrow A. Signals from a flowmeter 25 establish actual flow conditions that are transmitted to processor 61. A target flow may be established by adjusting the variable restrictor 81 to achieve the desired pulsation suppressed flow.

Figure 5:
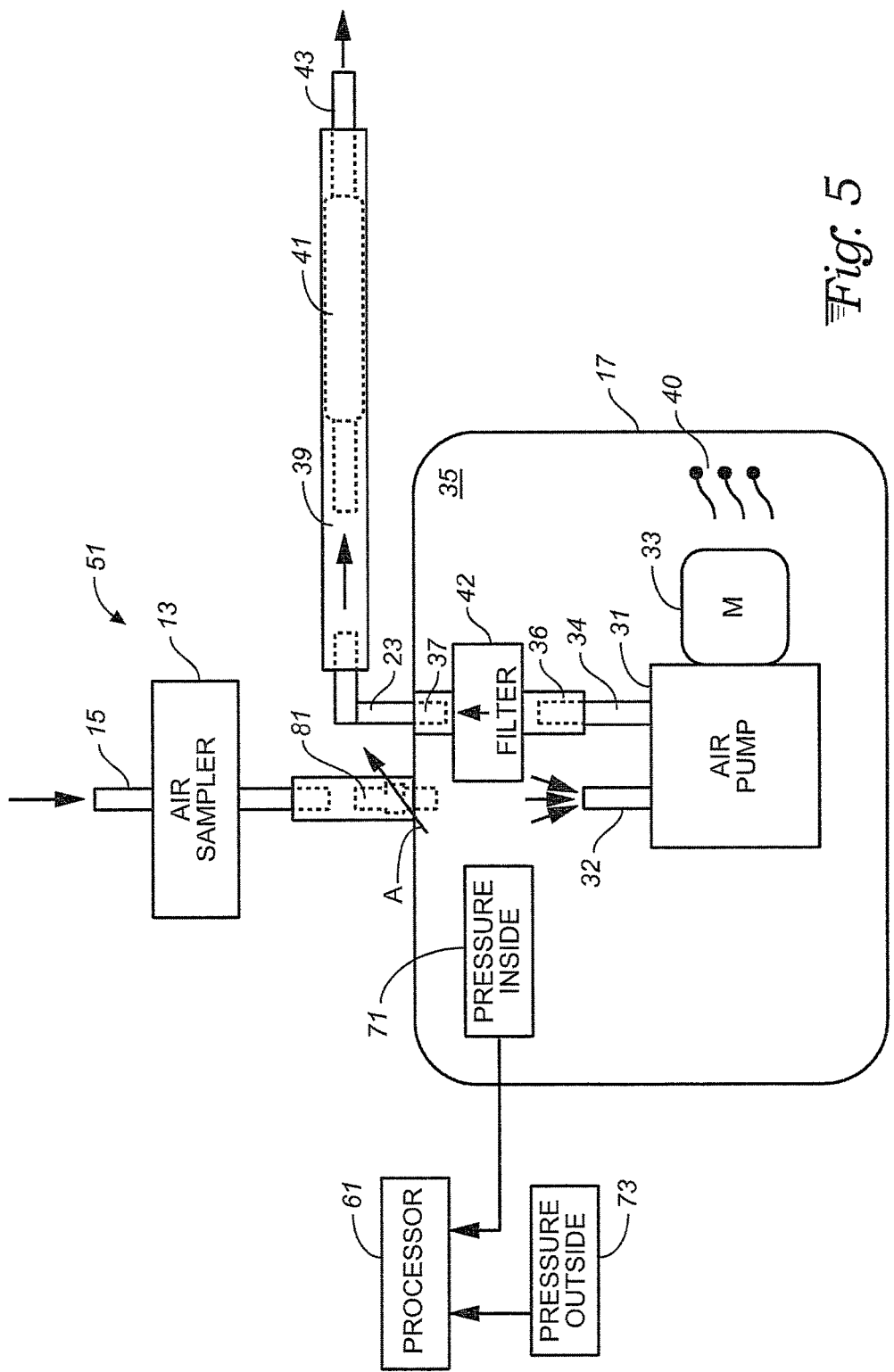
FIG. 5 is a plan view of a third alternate embodiment particle suppressing air flow system for an air sampling instrument of the invention with a variable flow restrictor controlled by pressure sensors.

FIG. 5 shows a variable restrictor 81 controlled by pressure sensors, rather than by a flowmeter. This was previously discussed with reference to FIG. 2. A pressure sensor inside of housing 17 measures the vacuum within the housing 17 while an outside pressure sensor 73 measures ambient pressure as flowing into the air sampling instrument 13 through the air intake 15. The variable restrictor 81, which may be a variable valve, is controlled by processor 61 using differential pressure measurements, inside of housing 17 and outside, in order to adjust the volumetric air flow. The surge chamber 35 operates as previously described to suppress pulsations in the air flow being pulled into the air intake 15 of the air sampling instrument 13. A particle filter such as a HEPA filter 42 removes particles that come from within pump 31 and motor 33. Particles 40 external to the pump and motor which are shed by the apparatus are trapped within the housing 17. Air evacuated from the chamber exits the housing through the output conduit 39, an output filter 41 and exhaust port 43.

EXAMPLE

Pump flow rate: 0.1 CFM
Surge chamber volume (less internal hardware): 7.8 cubic inches
Housing size: approximately 2.65×3.75×1.59 inches, volume approximately 16.2 inches (internal housing volume)
Pump volume: approximately 4.26 cubic inches (space occupied by the pump)
Flow restrictor: 0.030 inch diameter
Bypass orifice: 0.016 inch diameter
Vacuum inside surge chamber: 25 inches of H20, or about 0.9 PSI
Exhaust filter rating: 0.01 micron at 99.99%

Figure 6:
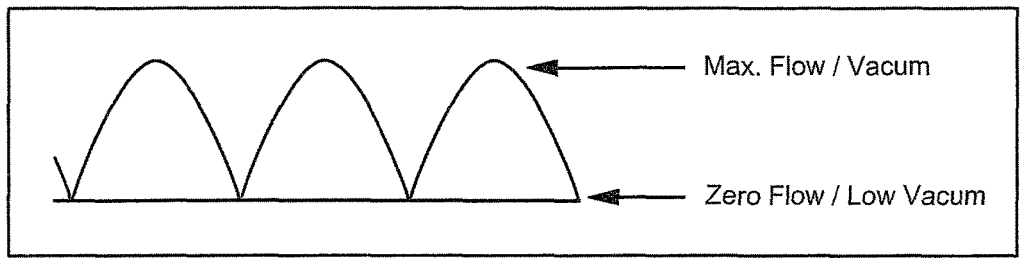
FIGS. 6-8 are plots of pressure and flow for pumps for use in housings of the type shown in FIGS. 1, 2, 4, and 5.

With reference to FIG. 6 surges are illustrated for a typical pump at the pump inlet to be used with an air sampling instrument. For reciprocating pumps, the pump inlet has large flow to vacuum surges that go from zero to maximum flow to vacuum.

Figure 7:
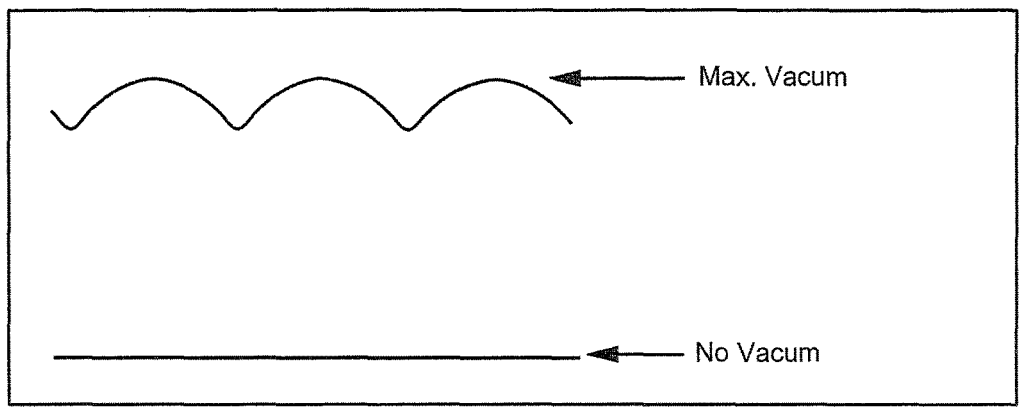

With reference to FIG. 7, pressure variations are illustrated using the surge chamber of the present invention. The pressure difference across the restrictor (vacuum on one side and ambient on the other) results in air flow through the restrictor. The resulting flow pulsations are proportional to the surge chamber vacuum pulsations.

Figure 8:
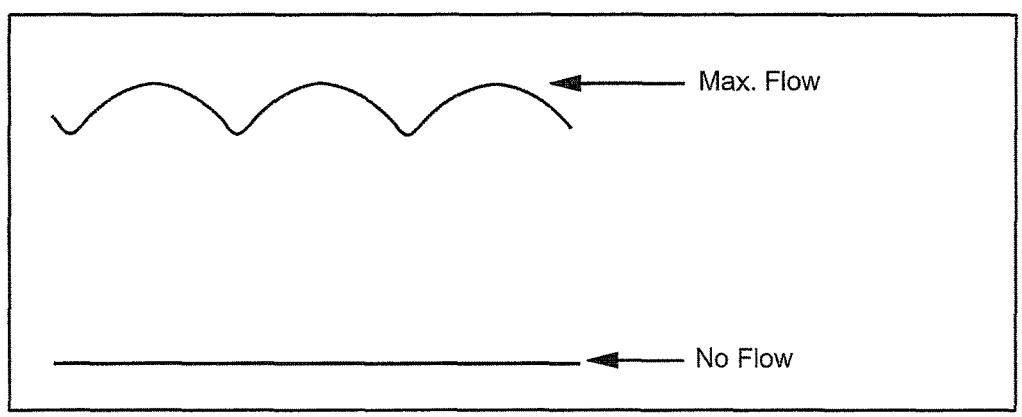

The pressure variations of FIG. 7 translate to the flow variations of FIG. 8 using the present invention. As seen in FIG. 8, the flow pulsations are much smaller than the pulsations at the pump inlet in FIG. 6. A particle counter (air sampling instrument) uses a flowmeter to regulate the average flow. To get more flow, the pump runs faster pulling a higher vacuum in the surge chamber. If one increases the restrictor orifice, the flow pulsations would become away from the baseline resulting in a smaller percent of flow; however, pump power dissipation would increase. A larger chamber will produce smaller flow pulsations and a smaller chamber will produce larger pulsations. A good engineering design would achieve an acceptable balance between flow pulsations overall size, pump power and pump life in accordance with the teachings herein.

While the present invention both suppresses pulsations of air flow coming into the air sampling instrument 13, as well as trapping particles, additional benefits exist. There is a sound reduction benefit because vibration from the motor and pump noise are mainly within the housing 17. Under vacuum conditions, the sound is not transmitted by air, but only by the support structure. The present invention has the surge chamber within the housing which would eliminate tubing and fittings required to connect a separate external surge chamber and separate external restrictor. The present invention is not limited to particle counters and particle sensors, but could be used in any scientific instrument requiring continuous pulsation and particle suppressed air flow.

What is claimed is:

1. A particle suppressing air flow system for an air sampling instrument requiring continuous air flow therethrough comprising:
   a housing having a sealed volume with an entrance air inflow port and an exit airflow port;
   an air pump having a non-uniform pumping characteristic, the pump occupying a portion of the volume of the housing in a sealed manner, the unoccupied portion of the volume constituting a surge chamber, and having an air inlet spaced from the entrance air inflow port and having an outlet connected to the exit airflow port, the pump having the non-uniform pumping characteristic that reduces pressure to a first pressure in the surge chamber below a second pressure outside of the housing; and
   the air sampling instrument associated with a flowmeter connected to the air inflow port of the sealed housing;
   whereby the non-uniform pumping characteristic of the pump is damped by the surge chamber to produce uniform, continuous air flow through the air sampling instrument.

2. The apparatus of claim 1 wherein the air sampling instrument is a particle counter.

3. A pulsation suppressing air flow system for an air sampling instrument requiring continuous air flow therethrough comprising:
- a housing having a sealed volume with an entrance air inflow port and an exit airflow port;
- an air pump having a non-uniform pumping characteristic occupying a portion of the volume of the housing in a sealed manner, the unoccupied portion of the volume constituting a surge chamber, and having an air inlet spaced from the entrance air inflow port and having an outlet connected to the exit airflow port, the pump having the non-uniform pumping characteristic that reduces pressure to a first pressure in the surge chamber below a second pressure outside of the housing, with a two sided flow restrictor in the entrance air inflow port that establishes a vacuum that pulls a continuous airflow into the surge chamber through the air inflow port with the first pressure on one side of the restrictor and the second pressure on the opposite side of the restrictor;
- the air sampling instrument associated with a flowmeter connected to the air inflow port of the sealed housing; and
- a particle filter associated with the exit airflow port of the housing trapping particles generated by the pump within the housing;
- whereby the non-uniform pumping characteristic of the pump is throttled by the restrictor acting with the surge chamber to produce uniform, continuous air flow through the air sampling instrument.

4. The apparatus of claim 3 wherein the air pump is a reciprocating pump or a rotary vane pump.

5. The apparatus of claim 3 wherein the air sampling instrument is a particle counter.

6. A method of generating a continuous air flow from an air pump comprising;
- supporting the continuously operating air pump of the type having repetitive surges in an air stream inside of a sealed housing wherein the pump occupies a portion of the housing in a manner causing a lower pressure inside of the housing than ambient pressure outside of the housing when the air pump is in use;
- providing an air intake to the housing spaced a distance from the air pump wherein the distance spans a portion of an unoccupied space of the housing forming a surge chamber, wherein the air pump receives air from the air stream in a manner where surges are diluted across the distance to the air intake via the surge chamber;
- providing a filtered air exhaust from the housing in piped airflow communication with the pump; and
- operating the air pump so as to generate continuous air flow through the air intake, wherein surges of the air pump being taken into the housing are suppressed by the surge chamber.

7. The method of claim 6 further defined by providing feedback from a flowmeter to the air pump to regulate air flow amounts.

8. The method of claim 6 further defined by connecting an air sampling instrument to the air intake of the housing.

9. The method of claim 6 further defined by measuring pressure inside and outside of the housing to establish a pressure differential and then using the pressure differential to regulate air flow in the housing.

10. Apparatus generating continuous airflow for an air sampling instrument having a pump with surges comprising:
- a sealed housing in ambient air having an internal volume and the pump of specified air pumping flow rate supported therein, the pump having pump surges in normal operation and occupying only a portion of the housing internal volume, the housing having a restricted size air intake port and an air exhaust port extending outside of the housing, the air intake port connected to the associated air sampling instrument and spaced from the pump, with the pump having a pump intake spaced apart from the housing air intake port defining a surge chamber therebetween in the internal volume of the housing, with the restricted size air intake port and air pumping flow rate permitting pressure of the internal volume of the housing to be reduced compared to ambient air, thereby establishing a pressure difference, wherein the pumping surges are dampened by the surge chamber from the air intake port and the associated air sampling instrument.

11. The apparatus of claim 10 wherein the air intake port has a restrictor member in the restricted size air intake port.

12. The apparatus of claim 11 wherein the restrictor member is variable.

13. The apparatus of claim 10 wherein a flowmeter is connected to the air intake port.

14. The apparatus of claim 13 wherein a processor is connected to the flowmeter and to the pump.

15. The apparatus of claim 10 wherein pressure transducers are disposed inside and outside of the housing, the pressure transducers connected to controller means for regulating the air pumping flow rate of the pump.

16. The apparatus of claim 10 wherein the air exhaust port is connected to an air filter.

17. The apparatus of claim 10 wherein the air sampling instrument is a particle counter.

18. The apparatus of claim 10 wherein the pump is a rotary vane pump.

19. The apparatus of claim 10 wherein the pump is a reciprocating pump.

* * * * *